United States Patent [19]

Thomas

[11] Patent Number: 5,480,803
[45] Date of Patent: Jan. 2, 1996

[54] APPARATUS FOR TREATING ANALYTES

[75] Inventor: Nicholas Thomas, Cardiff, United Kingdom

[73] Assignee: Amersham International PLC, Buckinghamshire, United Kingdom

[21] Appl. No.: 923,807

[22] PCT Filed: Feb. 28, 1991

[86] PCT No.: PCT/GB91/00308

§ 371 Date: Jul. 22, 1993

§ 102(e) Date: Jul. 22, 1993

[87] PCT Pub. No.: WO91/13345

PCT Pub. Date: Sep. 5, 1991

[30] Foreign Application Priority Data

Mar. 1, 1990 [GB] United Kingdom ............ 9004596

[51] Int. Cl.$^6$ ............................................. C25D 1/12
[52] U.S. Cl. .................... 435/286.1; 204/299 R; 435/4; 435/6; 435/286.5; 435/287.2
[58] Field of Search ............................. 435/287, 312, 435/86, 4; 436/44; 354/302, 303, 301, 312; 101/116, 117, 118, 119, 120, 157, 169; 68/148, 152; 118/416, 426; 204/299 R

[56] References Cited

U.S. PATENT DOCUMENTS

| | | | |
|---|---|---|---|
| 2,031,010 | 2/1936 | Simjian | 95/94 |
| 3,435,835 | 4/1969 | Hobbs | 134/108 |
| 4,222,843 | 9/1980 | Suzuki et al. | 204/299 R |
| 4,248,514 | 10/1979 | Watkins | 354/299 |
| 4,982,326 | 1/1991 | Kaneko | 364/413.01 |

*Primary Examiner*—W. Gary Jones
*Assistant Examiner*—Scott Houtteman
*Attorney, Agent, or Firm*—Wenderoth, Lind & Ponack

[57] ABSTRACT

An apparatus includes an enclosed chamber in which a motor-driven cylinder is mounted for rotation about a horizontal axis. The lower half of the cylinder is disposed in a trough. A blot can be attached, analyte side outward, to the surface of the cylinder, and the cylinder is then rotated to carry the blot through a succession of treatment liquids, with which the trough is charged. Each liquid is discharged from the through before the next liquid is supplied. The liquid in the through can be maintained at any desired temperature above the ambient temperature. Water can be sprayed onto the blot to wash a liquid off and to flush the trough. The blot may be held in position on the cylinder by rollers which engage only the side edges of the blot.

21 Claims, 3 Drawing Sheets

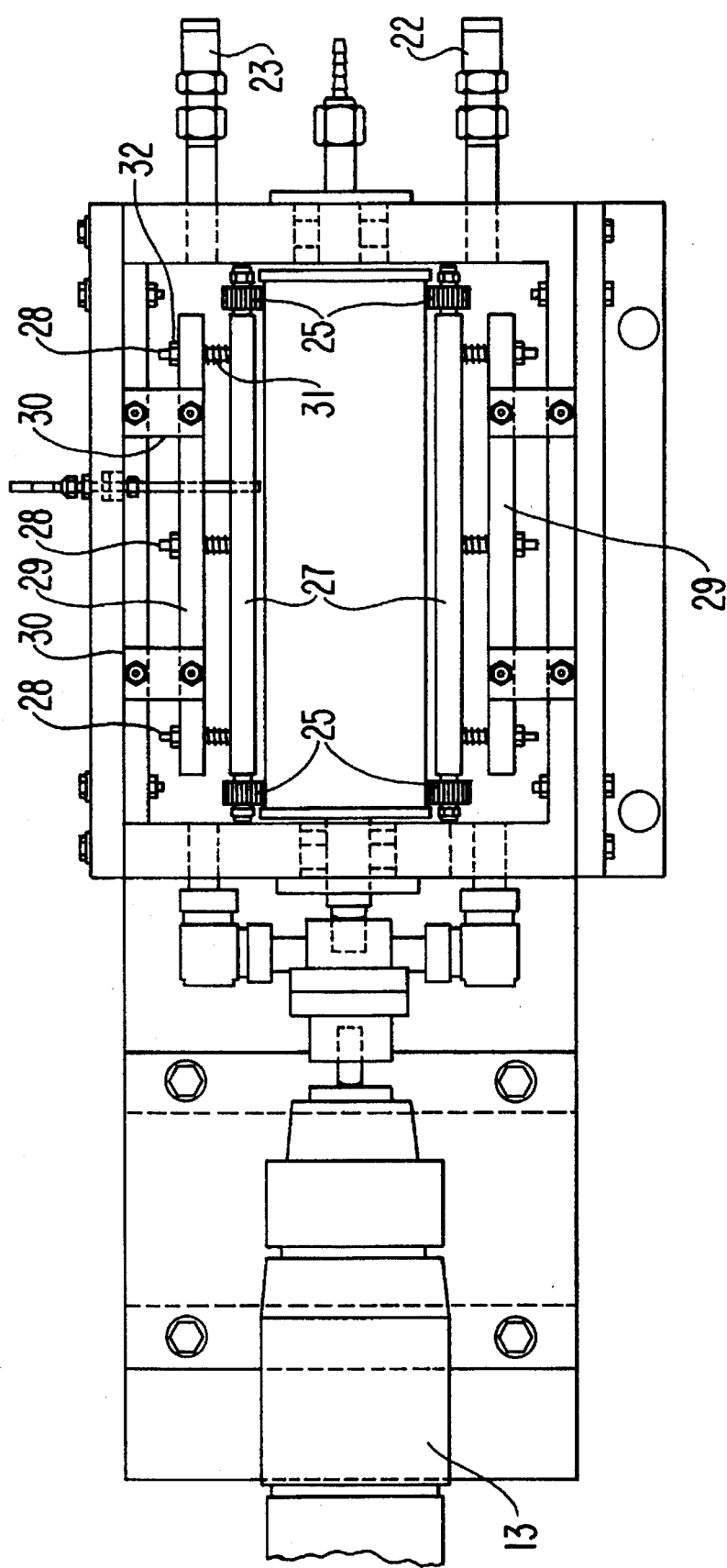

APPARATUS FOR TREATING ANALYTES

BACKGROUND OF THE INVENTION

This application is the national filing of PCT application No. PCT/GB91/00308.

It is common practice in the fields of biomedicine and molecular biology to use techniques for the analysis of biological molecules where the analytes are immobilised on the surface of membrane filters. Such techniques are well documented in the scientific literature and have been used for the analysis of DNA, RNA and protein molecules. The processes used in such analyses are commonly termed Southern blotting (1) where DNA molecules or fragments are analysed, Northern blotting (2) where RNA molecules or fragments are analysed and Western blotting (3) where proteins or polypeptides are analysed.

The principle of all these techniques involves separation of the analyte molecules by electrophoresis in agarose or acrylamide gels such that the molecules or fragments of molecules are separated according to their molecular weight or physical size. Separation is followed by transfer of the analyte to a membrane composed of natural or synthetic polymer to produce an exact replica of the separation pattern on the gel. Such transfer is commonly achieved by capillary transfer, application of an electric field or by use of vacuum suction.

In addition to the above techniques there are a variety of further blotting procedures in common use in biomedicine and molecular biology. The technique commonly known as the unblot (4) process involves drying the gel used for separation of the analyte to form a thin sheet which can then be handled and treated identically to a membrane blot. The techniques known as dot blotting (5) and slot blotting (6) are also widely used to confirm the presence or absence of a particular molecule or molecular fragment in an unseparated analyte mixture. In these techniques the analyte is applied directly to the membrane filter, either by use of a pipette tip, or by using a manifold filtration device.

Further blotting techniques are used in the process of gene cloning, to identify organisms containing an inserted nucleic acid sequence. In these procedures, known as colony lifts where bacteria are the organism used, or plaque lifts where the organism is viral, a filter is laid on the surface of a culture plate containing the organism and then removed, forming a replica of the distribution of organisms on the culture plate, which is then analysed for the presence or absence of the inserted nucleic acid sequence.

Central to all of the above techniques is the requirement to expose the immobilised analyte to a solution containing a further biomolecule, commonly termed a probe, which has an affinity for one or more analyte molecules, such that the probe molecule is able to bind to the immobilised analyte.

The probe molecule, which may be DNA, RNA, a synthetic oligonucleotide, a protein or polypeptide, or a ligand, is labelled with a radioactive isotope or non-radioactive reporter molecule, which may be either an enzyme or a small molecule (typically biotin or a hapten) recognised by an antibody or other binding protein.

Following exposure to the probe the blot is washed in order to achieve removal of unbound probe. Where the probe is labelled with a radioisotope, exposure of the blot to X-ray film produces an image on the film corresponding to the location of the analyte molecule or molecules recognised by the probe.

Where the probe carries a non-isotopic label further stages are necessary to achieve localisation of the bound probe. In the case of enzyme labelled probes, addition of a specialised enzyme substrate solution leads to the formation of a coloured stain or the emission of light at the position of the probe. Where the probe is labelled with biotin or a hapten molecule the blot is exposed to a solution containing either avidin or steptavidin in the case of biotin labelled probes, or to a solution containing an antibody recognising the hapten molecule. The antibodies or biotin binding proteins used in these procedures may themselves be labelled with either a radioisotope or an enzyme label, and detection is achieved using X-ray film or an enzyme substrate as described above.

While the great number of probe detection systems vary widely in method of action and in the complexity of the techniques used, all systems share a common requirement for multiple exposure of the immobilised analyte to reagent solutions, with each exposure separated by a washing procedure to prevent carry over or to remove non-specific binding of reagent, and to prevent interference with the next stage in the detection process.

Conventional methods of processing membrane blots to detect analytes are well established and documented (7,8,9, 10). All methods rely on using a container or chamber in which the blot is placed, and into which the necessary reagent solutions may be introduced, in order to effect the desired detection of the analyte.

Such containers or chambers are typically plastic bags, plastic boxes, or plastic or glass tubes, or various combinations of containers may be used in a single procedure. The use of such containers is well documented in the scientific literature, and a variety of commercially produced apparatus are available.

Currently available methods all rely on varying degrees of manual intervention during the process of probing and detection of probe, and require the worker to carry out manual addition and removal of the various reagents used. As a consequence, the techniques used are labour intensive, time consuming and unsuitable for automation due to the intricacy of the manipulations involved in transfer of membranes in and out of containers, and in addition and removal of reagents without causing damage to the blot.

The invention as described seeks to remove the need for manual handling of the blot during processing and to perform the process of detection of analyte automatically by introduction of all necessary reagent and washing solutions onto the blot. Furthermore, by inclusion of a blot feed mechanism the invention may be used to allow the automatic sequential processing of a number of blots according to programmed instructions.

SUMMARY OF THE INVENTION

According to this invention in one aspect there is provided apparatus for handling or processing an analyte carried by a transporting means, comprising a processing chamber, a horizontally-disposed motor-driven rotary drum mounted in the chamber, means for attaching the transporting means to the peripheral surface of the drum, said chamber including a bath into which the lower portions of the periphery of the drum dip, and means whereby liquids can be fed into and emptied from the bath characterized in that the drum has means whereby the transporting means is releasably attached by only its transverse leading edge to the drum, and in that the bath is shaped and arranged to extend closely about the lower portions of the periphery of the drum.

According to this invention in another aspect there is provided a method of treating a membrane blot comprising mounting the blot in a mesh envelope of sufficient porosity to allow free access to liquid reagents, attaching the mesh envelope by only its leading edge to a motor-driven horizontally disposed rotary drum, placing in a bath extending closely about the lower portions of the periphery of the drum a succession of liquid treating and washing agents in turn each agent being discharged from the bath before the next agent is admitted, and rotating the drum to carry the envelope and blot through the liquids in the bath.

The invention also provides a method of treating a membrane blot carried by a carrier sheet of solid phase material comprising the steps of attaching the carrier sheet to a rotary element at least part of the periphery of which is disposed in a bath in which a succession of liquid treating and washing agents are accommodated in turn, each agent being discharged from the bath before the next agent is admitted, and rotating the rotary element whereby the blot is carried through the liquids in the bath in succession.

In a convenient application of the method of this invention membranes carrying the biological analyte or analytes are processed in a mechanism utilising a rotating drum, partially bathed in reagent solutions. Blots are held, analyte side outwards, on the central drum by attachment of the leading edge of the blot to the drum, and hence all areas of the blot are continually bathed with processing reagents as the blot is passed through the solutions by the rotating action of the drum.

Blots to be processed by this method may be of a standard size, determined by the dimensions of the processing drum or, alternatively, one or more smaller blots may be processed by use of a transporter in the form of a mesh envelope adaptor of a size suited to the dimensions of the drum. Where non-standard blots are used, one or more blots are placed in a heat sealable nylon mesh envelope of the same dimensions as the standard blot, the envelope sealed by heat welding, and processed in the same way as a standard blot.

DETAILED DESCRIPTION OF THE DRAWINGS

In order to clarify the principle and function of the invention, reference is now made to the accompanying drawings in which:

FIG. 3 shows a plan view of the apparatus of FIG. 1; and

DETAILED DESCRIPTION OF THE INVENTION

Figure 1:
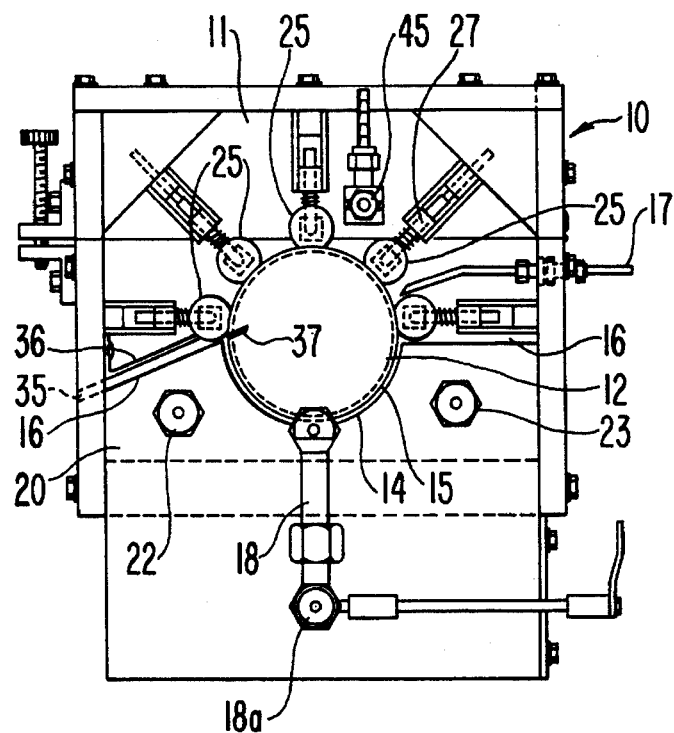
FIG. 1 shows an end elevation of a processing apparatus according to the invention.
Figure 4:
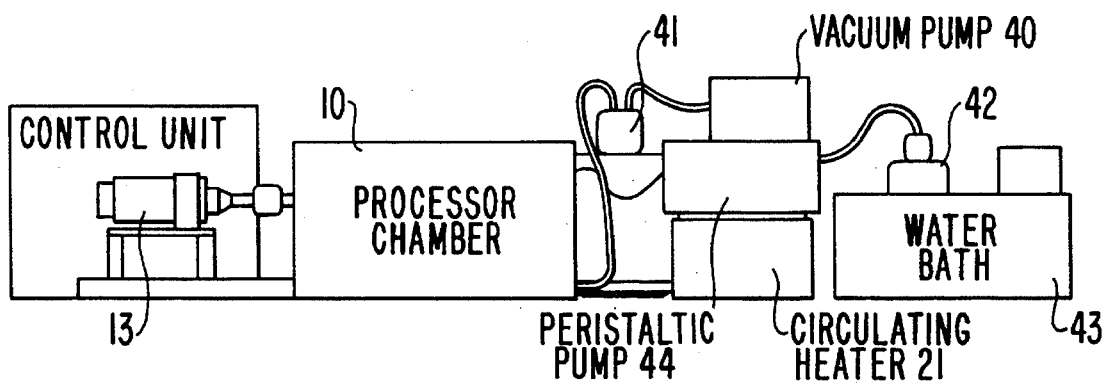
FIG. 4 shows the apparatus of FIGS. 1 to 3 with ancillary equipment.
Figure 2:
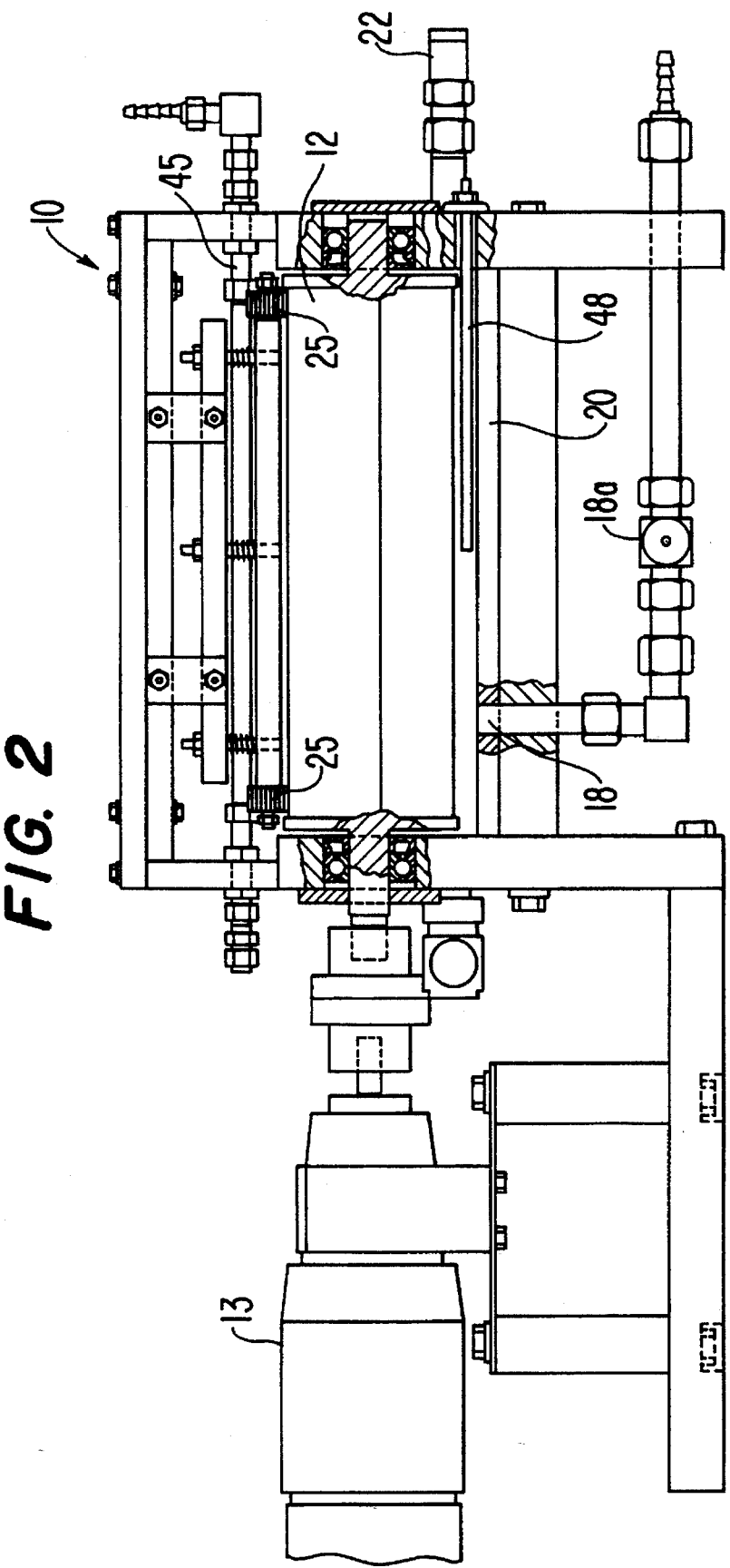
FIG. 2 shows a front elevation of the apparatus of FIG. 1.

Referring to FIGS. 1 to 4 of the drawings, the apparatus comprises a casing 10 providing, in its upper portions, a chamber 11 in which a drum 12 driven by an electric motor 13 is mounted for rotation about horizontal axis. A semi-cylindrical wall 14 extends substantially coaxially with the drum about the lower half of the drum and is spaced from the surface of the drum to form therewith a semi-annular space 15 which forms a bath or treatment chamber. Lateral continuations 16 of the semi-cylindrical wall 14 extend outward to the casing to form a sealing partition across the chamber. The axial ends of the walls 14,16 are sealed with respect to the casing. The space 15 can be charged with liquids through a feed pipe 17 projecting into the chamber 11 through the casing wall, and these liquids can be removed through an outlet duct 18 leading through the wall 14 from the bottom of the space and thence out of the casing, under the control of an outlet valve 18a which operates to seal the chamber 11, including the semi-annular space 15, during processing. The walls 14,16 form also the top of a water jacket 20 through which water at any predetermined temperature above the ambient value can be circulated by means of a circulatory pump, the water temperature being set by a thermostatically controlled heater 21. The inlet and outlet pipes for the circulating water are shown at 22 and 23.

In operation, a membrane blot is introduced analyte face upward into the casing through a slot 35 therein and the leading edge of the blot is fed between part of the top wall 16 and a guide bracket 36 into an axial slot 37 in the cylindrical surface of the drum 12, the analyte face of the blot facing outward on the drum.

Once the leading edge of the blot is located in the slot in the processing drum, the drive motor 13 is switched on to rotate the processing drum and cause the location slot to pass in an upward direction drawing the blot onto the periphery of the drum until all of the membrane blot is held on the surface of the drum, the wet membrane adhering adequately to the drum. The circumference of the drum is greater than the length of the blot, so that the blot is held on the drum with no overlap and will continue to rotate with the drum throughout the processing regime.

During processing, reagents are introduced into the chamber 15 through the reagent feed pipe 17 by use of a syringe or a peristaltic pump and are removed after the appropriate period through the waste outlet 18 by application of suction from a vacuum pump 40 connected through a liquid trap 41. Where the addition of wash solutions is required, these are introduced, from a reservoir 42 held in a water bath 43, by a second peristaltic pump 44 through a wash bar 45 located in the chamber 11 above the drum and extending along its length, such that wash solutions are sprayed downwards from holes formed along the length of the wash bar over the rotating blot to collect in the chamber 15.

During all operations the temperature of solutions in the chamber 15 may be monitored by means of a thermocouple 48 immersed in the liquid at the base of the chamber. The read-out from the thermocouple is displayed on a separate control panel which also contains electronic means to control the speed of the processor motor 13.

Under this arrangement, washing may be accomplished by introducing a fixed volume of wash reagent sufficient to partially to fill the chamber 15, rotating the drum and blot for a period of time and then removing the spent wash solution to waste, followed by repetition of the process as necessary. Alternatively, wash solutions may be introduced and withdrawn continuously to give a continuous downward flow of wash reagent.

All pipe connections for the supply and removal of reagents and heating water may be arranged on the end walls to allow units to be placed together to form an interconnected multi-unit system.

The processing of blots for detection of analyte, as described above, offers a number of advantages over conventional processing methods and apparatus.

a) The apparatus allows all processing steps to be carried out within a sealed unit without the worker handling or manipulating the blot.

b) All stages of processing are carried out within the same chamber.

c) The circular geometry of the system minimises the volumes of reagents required for processing, as only a small volume of liquid is required in the base of the processing chamber.

d) Efficient processing is achieved by the constant motion of the blot through the reagents.

e) Efficient washing of blots is achieved through spraying wash solutions over the entire blot area.

f) The construction of the processing chamber prevents any contact or mechanical damage occurring to the area of the blot carrying the analyte.

g) By provision of appropriate automatic control of reagent addition and withdrawal, the processing mechanism can operate without intervention.

h) By linking together multiple processing units in combination with such equipment a higher capacity system may be constructed.

In order to illustrate the function and performance of this particular embodiment of the invention in processing membrane blots, reference is made to the two following non limitative examples.

EXAMPLE 1

Phage lambda DNA (0.5 µg) was digested with the restriction enzyme Hind III and the resultant fragments separated by electrophoresis in a 1% agarose gel. The fragments were transferred to a positively charged nylon membrane, marketed by Amersham International plc under the trade name Hybond-N+, by capillary blotting (1). A non-radioactive DNA probe was prepared by labelling lambda DNA with horse-radish peroxidase, marketed by Amersham International plc under the name ECL Gene Detection System, using standard methods.

Prior to starting blot processing the processing chamber was heated to 42° C. by circulating heated water through the water jacket 20 and 75 ml of pre-hybridisation buffer, using the ECL Gene Detection System marketed by Amersham International plc, containing 0.5 molar NaCl and 5% casein, was added by injection from a syringe. Once the buffer had reached 42° C. the membrane blot was fed onto the drum 12 and rotated at 5 rpm for 75 minutes. Following prehybridisation the buffer was removed, 60 ml of fresh buffer containing the enzyme labelled probe (10 ng) was added to the processor and rotation continued for a further 2 hours to allow hybridisation to occur.

Following hybridisation, the blot was washed following standard procedures, namely the ECL Gene Detection System marketed by Amersham International plc, using the peristaltic pump 44 (running at 500 ml/minute) to supply wash solutions (80 ml/wash cycle) to the chamber 15 through the wash bar 45 and removing spent wash solutions by means of the vacuum pump 40 and liquid trap 41. On completion of the wash procedure the blot was removed from the processor and soaked briefly in chemiluminescence substrate solution, using the ECL Gene Detection System marketed by Amersham International plc, and the resultant light emission from the enzyme labelled probe recorded by exposure to X-ray film for 1 minute.

EXAMPLE 2

Human genomic DNA (5 fg) was digested with the restriction enzymes alu I, ECor I, Hinf I and Hae III and the resultant digests separated by electrophoresis in a 1% agarose gel. DNA was transferred to a positively charged nylon membrane (Hybond-N+ marketed by Amersham International plc) by capillary blotting (1). A [$^{32}$P]-DNA probe was prepared by labelling a Y chromosome DNA repeat sequence with [$^{32}$p] -dCTP using random primer labelling marketed under the trade name Multiprime by Amersham International plc. Prior to blot processing the processing chamber was heated to 65xC by circulating heated water through the water jacket, and 75 ml of hybridisation buffer marketed under the trade name Multiprime Rapid Hybridisation Buffer by Amersham International plc was injected into the chamber. Once the buffer temperature had reached 65xC the membrane blot was fed onto the roller and rotated at 5 rpm for 15 minutes. Following prehybridisation the buffer was removed, 60 ml of fresh buffer containing the [$^{32}$P]-DNA probe (1 ng/ml) was added to the processor and rotation continued for a further 60 minutes to allow hybridisation to occur, Following hybridisation the blot was washed twice for 10 minutes in 0.3x SSC/0.1%SDS, using the peristaltic and vacuum pumps to supply and remove wash solution. On completion of the washing procedure, the membrane was removed from the processor, wrapped in Saran Wrap and hybridised probe located by exposure to autoradiography film, marketed under the trade name Hyperfilm-MP by Amersham International plc, overnight at −80° C.

The method of processing as described has considerable scope for automation. As the blot is not held within a sealed container it is possible to design a processing system where, following treatment of the blot with all necessary reagents, the blot is automatically removed from the processing drum 12 and ejected from the unit, so freeing the processor unit to accept, by manual or automated feeding, a further membrane for processing.

Such automated removal of blots may be achieved in the processing device described above by means of reversing the direction of rotation of the processing drum 12, and by use of a sliding or hinged flap, lifting the trailing edge of the blot from the drum and utilising the reverse rotation to feed the blot out through the entry slot in the reverse direction to that used to feed the blot onto the drum.

In a modification of the illustrated embodiment the central drum carries a magnetic strip or an electromagnet set into the surface of the drum along the linear axis, where such a magnet or magnets take the place of the locating slot 37 described above. In a device of this form the leading edge of the blot to be processed would carry a flexible magnetic strip, or a flexible strip of magnetically attractive material, allowing the attraction of the two magnetic surfaces to secure the leading edge of the blot onto the drum.

Utilising magnetic attachment of the blot allows the leading edge to remain on the surface of the drum, rather than hidden in a locating slot, and hence is accessible to allow removal of the blot without reversal of the rotation of the drum. Removal of the blot may be achieved in a similar means to that described above, where a sliding or hinged flap is used to detach the leading edge of the blot and hence allow removal from the drum. Where an electromagnet is used to attach the leading edge of the blot, blot removal may be accomplished by either de-energising the magnet, in which case the blot is no longer attached to the drum and may be removed by a flap as described above, or alternatively the polarity of the magnet may be reversed, so inducing repulsion between the blot and the drum, and so aiding removal of the blot from the drum.

The facility to remove blots automatically after processing allows the potential for a completely automated blot processing system in which blots are fed from a storage device into one or more processing units, and following treatment are ejected either into a further storage device to await manual detection of bound probe or alternatively to an automated detection or image analysis instrument.

LITERATURE CITED

1. Southern E. M. (1975) J. Mol. Biol. 98 503
2. Alwine J. C. et al (1977) Proc. Nat. Acad. Science USA 74 5350
3. Towbin H. et al (1976) Proc. Nat. Acad. Science USA 76 4350
4. Purrello M. and Balazs I. (1983) Anal. Biochem. 128 393
5. Hawkes R. et al (1982) Anal. Biochem. 119 142
6. Towbin H. and Gordon J. (1984) J. Immunol. Methods 72 313
7. Thomas N. et al (1988) Anal. Biochem. 170 393
8. Maniatis T. et al Molecular Cloning—A Laboratory Manual. Cold Spring Harbor (1982) pp 387–389
9. Wahl G. and Berger S. L. (1987) Methods in Enzymology 152 415
10. Meinkoth J. and Wahl G. (1984) Anal. Biochem. 267

I claim:

1. A method of treating a membrane blot comprising mounting the blot in a mesh envelope of sufficient porosity to allow free access to liquid reagents, attaching the mesh envelope by only its leading edge to a motor-driven horizontally disposed rotary drum, placing in a bath extending closely about the lower portions of the periphery of the drum a succession of liquid treating and washing agents, each agent being discharged in turn from the bath before the next agent is admitted, and rotating the drum to carry the envelope and blot through the liquids in the bath.

2. A method as claimed in claim 1, further comprising
   subsequent to completion of the treatment by said liquids, reversing the rotation of the drum and operating a flap to separate the trailing edge of the flap from the drum to enable the envelope to be released from the drum.

3. A method as claimed in claim 1, further comprising
   placing in the envelope a plurality of blots interleaved with layers of mesh material.

4. An apparatus for use in processing an analyte carried by a transporting medium, said apparatus comprising:
   a processing chamber;
   a bath wall mounted in said processing chamber and defining a bath container;
   a liquid inlet communicating with said bath container;
   a liquid outlet communicating with said bath container;
   a horizontally-disposed rotary drum rotatably mounted in said processing chamber and having a bottom portion thereof projected into said bath container such that a periphery of said drum is disposed adjacent but separated from said bath wall by a narrow gap; and
   a leading edge engagement means disposed on said rotary drum for releasably engaging only a leading edge of the transporting medium such that, upon rotation of said rotary drum, the transporting medium is pulled by its leading edge about said rotary drum and through said narrow gap.

5. An apparatus as claimed in claim 4, further comprising
   electric heater and/or cooling device for directly heating or cooling a liquid held in said processing chamber.

6. An apparatus as claimed in claim 5, wherein
   said electric heater and/or cooling device comprises an electrically heated or cooled water jacket.

7. An apparatus as claimed in claim 5, wherein
   said electric heater and/or cooling device comprises a water jacket supplied with water from an external circulating thermostatic source.

8. An apparatus as claimed in claim 4, wherein
   said leading edge engagement means comprises an axial slot formed in the periphery of said rotary drum.

9. An apparatus as claimed in claim 4, wherein
   said leading edge engagement means comprises an axially extending magnetic strip mounted at the periphery of said rotary drum.

10. An apparatus as claimed in claim 4, further comprising
    the transporting medium; and
    wherein said transporting medium includes a mesh envelope of sufficient porosity to allow free access to reagents, in which envelope the analyte is carried on a membrane blot or blots.

11. An apparatus as claimed in claim 10, wherein
    said envelope has a plurality of layers of mesh internally thereof with which layers of blots can be interleaved.

12. An apparatus as claimed in claim 4, further comprising
    the transporting medium; and
    wherein said transporting medium comprises a blot having a magnetic strip extending along a leading edge thereof for attachment of the leading edge to said drum.

13. An apparatus as claimed in claim 8, further comprising
    the transporting medium; and
    wherein the transporting medium comprises a blot having its leading edge reinforced by a flexible strip for engagement in said slot in said rotary drum.

14. An apparatus as claimed in claim 4, further comprising
    removing means for removing the transporting medium by reversing the direction of rotation of said drum to allow removal of the transporting medium in a direction opposite to that used to feed the transporting medium onto the drum.

15. An apparatus as claimed in claim 14, wherein
    said removing means comprises a flap for lifting a trailing edge of the transporting medium during reverse rotation of said drum to separate the transporting medium from said drum.

16. A system comprising a first apparatus for use in processing an analyte carried by a transporting medium, and a second apparatus, operably connected to said first apparatus, for use in processing an analyte carried by a transporting medium, wherein each of said first and second apparatus comprises:
    a processing chamber;
    a bath wall mounted in said processing chamber and defining a bath container;
    a liquid inlet communicating with said bath container;
    a liquid outlet communicating with said bath container;
    a horizontally-disposed rotary drum rotatably mounted in said processing chamber and having a bottom portion thereof projected into said bath container such that a periphery of said drum is disposed adjacent but separated from said bath wall by a narrow gap; and a leading edge engagement means disposed on said rotary drum for releasably engaging only a leading edge of the transporting medium such that, upon rotation of said rotary drum, the transporting medium is pulled by its leading edge about said rotary drum and through said narrow gap.

17. A system claimed in claim 14, further comprising an external unit for supplying reagents under automatic control, said external unit being communicated with said liquid inlet of at least one of said first and second apparatus.

18. The system as claimed in claim 16, wherein said first apparatus is disposed in series with said second apparatus.

19. The system claimed in claim 16, further comprising a feeder mechanism capable of automatic feed of blots to said first and second apparatus.

20. The system claimed in claim 19, further comprising an automated imaging system operably connected to at least one of said first and second apparatus.

21. The system claimed in claim 20, further comprising a computerized image analysis system connected to said automated imaging system.

\* \* \* \* \*